United States Patent [19]

McDonald et al.

[11] 4,211,658

[45] Jul. 8, 1980

[54] TRIAXIALLY COMPRESSED PACKED BEDS

[75] Inventors: Patrick D. McDonald, Holliston; Richard V. Vivilecchia, Hopkinton; David R. Lorenz, Milford, all of Mass.

[73] Assignee: Waters Associates, Inc., Milford, Mass.

[21] Appl. No.: 961,747

[22] Filed: Nov. 17, 1978

Related U.S. Application Data

[63] Continuation of Ser. No. 867,442, Jan. 6, 1978, abandoned.

[51] Int. Cl.[2] .............................................. B01D 15/08
[52] U.S. Cl. .................................... 210/198 C; 55/386
[58] Field of Search ................. 210/31 C, 198 G, 332, 210/466–468, 484; 55/386, 67

[56] References Cited

U.S. PATENT DOCUMENTS

| | | | |
|---|---|---|---|
| 2,394,895 | 2/1946 | Burhans | 210/484 X |
| 2,396,712 | 3/1946 | Luttge et al. | 210/484 |
| 3,570,673 | 3/1971 | Butz et al. | 210/198 C |
| 3,791,522 | 2/1974 | Eisenbeiss et al. | 210/198 C |
| 4,059,526 | 11/1977 | Mochizuki et al. | 210/198 C |

*Primary Examiner*—John Adee

[57] ABSTRACT

A cartridge is disclosed which comprises a volume of particulate packing material through which a fluid is to flow, a piece of solid porous material adjacent to the surface of the packing material though which the fluid is to enter the volume and a second piece of solid porous material adjacent to the surface of the packing material through which the fluid is to exit from the volume, and a heat-shrinkable tubing which triaxially compress the packing material into a tightly packed bed predominantly in the directions which are normal to and parallel to the direction of fluid flow through the packed bed and which extends beyond the pieces of solid porous material to form an inlet opening to and an outlet opening from the packed bed.

12 Claims, 5 Drawing Figures

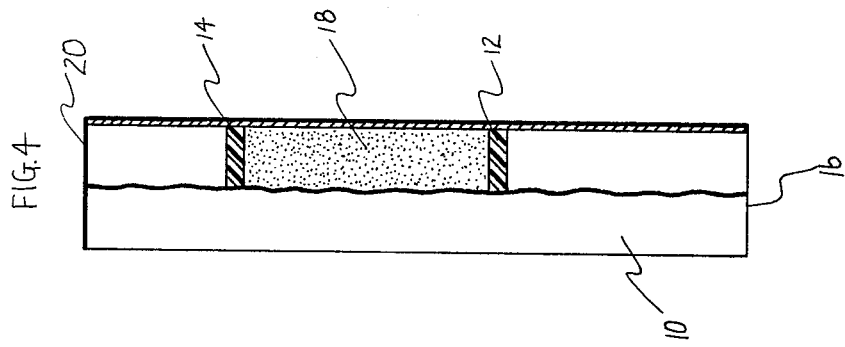
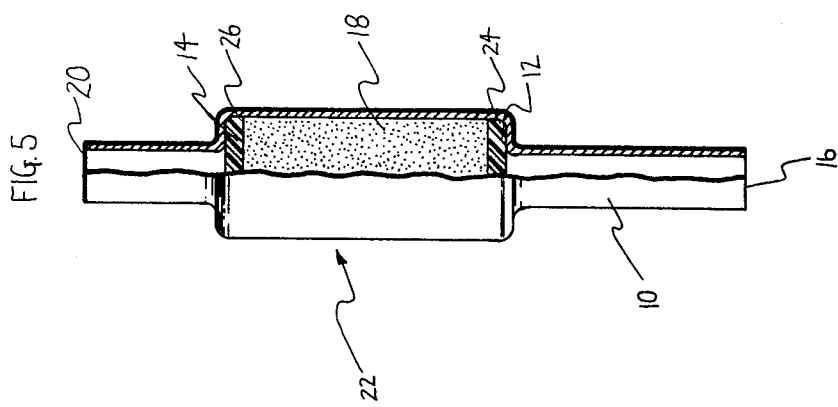

TRIAXIALLY COMPRESSED PACKED BEDS

This is a continuation of application Ser. No. 867,442, filed Jan. 6, 1978, now abandoned.

BACKGROUND OF THE INVENTION

1. Field of the Invention

This invention relates to improved packed bed apparatus and to the process for making such apparatus. More particularly, the invention relates to improvements in packed bed apparatus in which the packing material has been triaxially compressed.

2. Description of the Prior Art

Liquid chromatography is a process utilized in both preparative and analytical chemistry. Essentially, the process comprises the interacting of a mobile phase with a stationary phase. Typically, the stationary phase is a surface active powder such as silica, alumina, an inert size-separating material such as a gel-permeation chromatography packing, or the like. This powder is contained within a chromatographic column. The mobile phase, which generally consists of a carrier fluid and a sample of a chemical to be identified, analyzed or purified, is passed through the column. The process is typically utilized to separate various chemical compounds in an unknown sample. This separation is made by using a stationary phase which differentially retards the progress of the different components of the sample through the column so that these components are separated and leave the column at different times. The separation may also be achieved by an exclusion process based on the difference in sizes between molecules, for example by gel-permeation chromatography processes.

In order to achieve separation of sample components which are very close to each other in chemical and physical properties, highly sophisticated procedures have been developed in the many processing techniques associated with liquid chromatography. Special pumps and valves have been developed for presenting samples to the inlets of the chromatographic columns with as much integrity as is possible to avoid building into the process an initial and inherent dispersal of the sample which dispersal would tend to reduce the resolution capabilities of the packing within the chromatographic column. Much work has been done to provide flow-distributing devices at the inlets to the columns to assure the even placement of the samples across the cross-sectional areas of the columns. Also, a great deal of technical effort has provided improved chromatographic packings and highly sophisticated analytical apparatus for measuring various properties of the liquid effluent leaving the column.

Despite such work as has been described above, it has remained a problem to achieve an uniform packing of the chromatographic material within a column. Many techniques have been suggested including vibration. See, e.g. U.S. Pat. No. 3,300,849. All of these techniques require careful control if segregation of particles by size is to be avoided and uniformly packed columns are to be obtained. Even after the column is filled, problems exist in maintaining the packing in proper condition during transportation and operation of the packed columns. See U.S. Pat. No. 3,349,920.

In general, the most commonly used practice of filling a high-performance column has been a costly method including slurrying the packing and passing the slurry into the column, thereby using the column itself as a form for placing a closely packed bed of chromatographic packing therein. Despite this costly time-consuming method of column manufacture, shifting of the packing may occur during shipment if the column is subjected to various vibration and other transient non-predictable physical abuse. Shifting tends to cause voids in the packing within the column and such voids can wholly destroy the separation capability of a column. Such defects in columns with stainless steel walls are not usually detectable until a standard sample is measured as a control. Suppliers of quality chromatographic columns have individually pre-tested each column before shipment to the customer to assure that the packing was properly placed in the column. The procedure, however, provides no protection against the hazards encountered during shipment or during use by the customer.

A number of solutions have been suggested for holding the packing in place. Some of these, like the aforementioned vibration technique and slurrying technique, emphasize a maximum effort to put a conventional packing into a column in such a way as to have it assume a stable position. Other techniques such as those described in U.S. Pat. No. 3,808,125 use rather complex or expensive procedures for fastening the packing to the column wall.

None of these attempts by the prior art have been dependably successful in achieving consistently excellent chromatographic performance and long term bed stability from column to column at a cost which could make the apparatus available to the broadest spectrum of chromatographers.

Although the foregoing description of problems relating to chromatographic columns has been largely devoted to liquid chromatographic columns, it is emphasized that many of the problems described above also relate to gas chromatography, i.e. chromatography wherein the sample and mobile phase are in gaseous, rather than liquid, form. In many respects, the problems relate to all packed-bed apparatus comprising a porous mass of particles intended to be intimately and uniformly contacted by a fluid. Such apparatus includes catalytic beds for the treating of gas and liquid, packed beds used in ion exchange processes, in electrophoresis applications, and the like. It is intended that the invention described below be viewed as an improvement in packed-column preparation for all such processes; albeit, the invention will be seen to have particular advantage in the field of liquid chromatography.

In discussing column packing processes, it is helpful to recognize four kinds of space, all of which can be referred to as "void volume." These include (1) void volume inside a porous particle; (2) theoretical void volume between particles, i.e. the type of unavoidable volume which would result from a perfectly packed bed of spheres of the same size; (3) void volume between particles which is attributable to imperfect packing of particles, usually present to some extent in any actual packed structure and (4) void volume which represents relatively large voids resulting from the consolidation of those voids described in (3). Voids (4) substantially reduce resolution of a sample being subjected to chromatographic analysis.

The invention disclosed below is believed to be most useful in avoiding the occurrence of such void volume as described in (4). The present invention also tends to reduce void volume as described in (3); moreover, it makes such void volume more nearly uniform, and closer to the theoretical ideal (2). Void volume, as generally used herein relates to a composite of void volumes (3) and (4).

Some workers have suggested comression of the packing of a chromatographic column by force directed longitudinally, i.e. parallel to the direction of liquid flow. However, such a procedure is relatively ineffective probably because the packing tends to form bridges which interfere with propagation of the compression force downwardly throughout the length of the column. An example of longitudinal compression is described in the Journal of Chromatographic Science of October, 1974, in an article entitled "Description and Performance of an 8 cm i.d. Column For Preparative Scale High Pressure Liquid-Solid Chromatography" by Godbille and Devaux.

In copending U.S. application Ser. No. 848,752 filed Nov. 4, 1977, which is a continuation of Ser. No. 638,301 filed Dec. 8, 1975, we have described in detail a method of making chromatographic columns which obviates the difficulties encountered by the prior art methods discussed above and provides consistently uniformly packed chromatographic columns having improved quality and uniformity of separation characteristics from column to column. In the chromatographic columns disclosed in the application the packing material is radially compressed by applying a force predominantly in a direction which is normal to the direction of flow of the liquid through the column and to the longitudinal dimension of the packing. It is suggested that such radial compression may be achieved by mechanical and fluid means. In one embodiment a polymeric walled column is placed in a packing chamber and expanded, for example by air pressure and heating, filled with packing material and then radially compressed, for example by air pressure or by allowing the polymeric wall to cool and contract. Since shipment of the column may loosen the radial force on the packing, the column should be recompressed upon receipt by the user. This application discusses in detail numerous other ways in which the chromatographic packing can be radially compressed and therefore is incorporated herein by reference as though set out in its entirety herein.

U.S. Pat. No. 3,570,673 discloses a method for producing a separation column for use in liquid chromatography consisting of inserting a bundle of parallel inorganic fibers into a tube of chemically resistant material, shrinking the tube onto the bundle of fibers, and then forcing a solvent through the bundle to remove the soluble phase of the fibers and obtaining a porous fibrous body.

SUMMARY OF THE INVENTION

The prior methods of achieving radial compression of the packing in a chromatographic column have been greatly simplified in accordance with the present invention so that chromatographic columns having uniform packing and separation characteristics can be obtained easily and inexpensively.

In accordance with the present invention, packed bed apparatus in the form of cartridges are prepared from a piece of heat-shrinkable tubing, two pieces of solid porous material, and a small quantity of particulate packing material. A cartridge is made by placing a piece of solid porous material into one end of a piece of heat-shrinkable tubing so that the piece of solid porous material is recessed from the end of the tubing. A small amount of packing material is then placed into the tubing against the inside surface of the porous material and the tubing is tapped briefly to settle the packing slightly. A second piece of solid porous material is then placed into the other end of the tubing and pressed snugly against the surface of the packing material. The assembly is then heated to cause the tubing to shrink tightly around the outer surfaces of the pieces of solid porous material and packing material. During the shrinkage of the tubing, force is applied to the pieces of solid porous material and packing radially as well as longitudinally, causing the packing material to be triaxially compressed. Chromatographic cartridges which have been triaxially compressed in this manner have been found to be uniformly and homogeneously packed so that they exhibit reproducible and uniform separation characteristics. The longitudinal force which is applied to the pieces of the porous material prevents the longitudinal dimension of the bed from changing thereby permitting the radial shrinking of the tubing to compress the packing material to form the bed.

The term "triaxial compression" as used in this specification means compression predominantly in the directions which are normal to and parallel to the direction of fluid flow through the packed bed.

BRIEF DESCRIPTION OF THE DRAWING

FIG. 4 illustrates the piece of heat shrinkable tubing of FIG. 3 after the placement of a second piece of solid porous material therein.

FIG. 5 illustrates the piece of heat shrinkable tubing of FIG. 4 after heat shrinkage.

DESCRIPTION OF THE PREFERRED EMBODIMENTS

Figure 1:
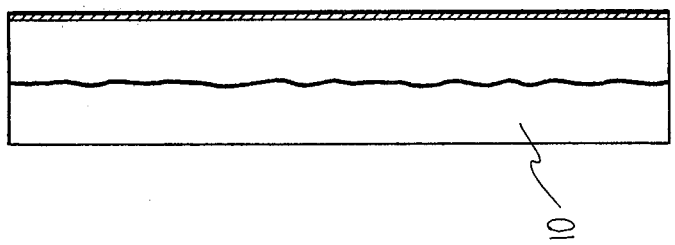
FIG. 1 illustrates a piece of heat shrinkable tubing prior to placement of the two solid pieces of porous material and the packing material therein.

An important element used in preparing triaxially compressed packed bed cartridges is heat-shrinkable tubing. Any tubing material which shrinks sufficiently upon heating to apply the required compressive forces on the pieces of solid porous material and packing material may be used. Examples of such tubing material are irradiated polyolefins, and polytetrafluoroethylene. It is preferred that heat-shrinkable, irradiated, cross-linked, low density polyethylene tubing be used for the preparation of triaxially compressed cartridges. The low density polyethylene tubing is preferred because of its chemical resistance, elasticity, resistance to stress cracking and low cost.

The packing material which is placed inside the heat-shrinkable tubing can be selected from any of the well-known packing materials used in packed bed apparatus. The particular packing employed will depend on the type of application for which the cartridge is to be used such as a chromatographic bed, a catalytic bed, an ion exchange bed, and electrophoresis bed, a bio-affinity bed, or a chemically reactive bed. Suitable chromatographic packing materials include silica gel, octadecylsilane-bonded silica, and any of the other well-known chromatographic packings.

The pieces of solid porous material which are placed on both ends of the packing material inside the heat-shrinkable tubing can be made from any of the well-known solid porous materials with a porosity suitable for retaining the packing material. For example, suitable porous materials include chemically resistant porous polymers such as high density polyethylene or polytetrafluoroethylene, ceramics, and metals or combination layers thereof.

The process for preparing chromatographic cartridges described herein can be used to prepare any packed bed apparatus in which a porous mass of packing material is to be intimately and uniformly contacted with a liquid or gas fluid and it is desired that the bed be uniformly packed. These cartridges, however, are particularly useful in sample preparation. As used herein, the term "sample preparation" refers to the use of a chromatographic bed to extract, concentrate, enrich, filter, or purify a component or components present in a complex sample matrix prior to final analysis by liquid chromatography, gas chromatography, mass spectrometry, or the like.

A sample preparation cartridge is not designed as a high efficiency analytical column, but rather as a homogeneous bed used to effect simple separations of a complex matrix and to smplify the final quantitative analysis of particular components in that matrix. It is intended to be used once and discarded, since reuse in a quantitative analytical scheme might lead to false measurements.

Because of its simple construction, the cartridge can be easily tailor-made for specific applications. For example, various layers of packing materials can be placed in the cartridge to achieve very specific separations or to perform specific functions which are dependent upon the requirements of the analysis. A layer of sodium sulfate or other dessicant, for example, can be used to dry an organic extract of an aqueous matrix before the extract passes into an active silica layer. A solid porous material may be used to separate layers where mixing is undesirable. The cartridge can also be used as a disposable sample filter by inserting a filter element into the heat-shrinkable tubing.

Figure 2:
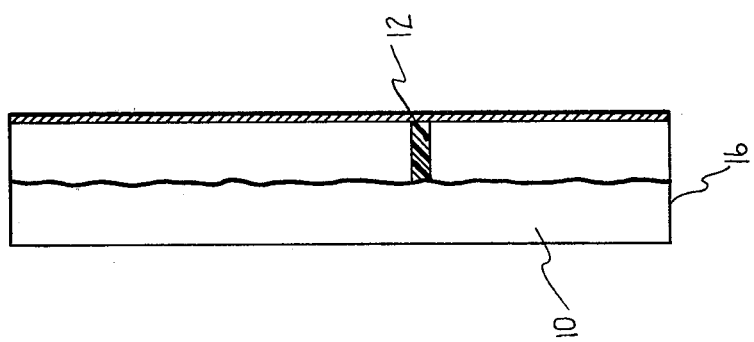
FIG. 2 illustrates the piece of heat shrinkable tubing of FIG. 1 after the placement of a piece of solid porous material therein.
Figure 3:
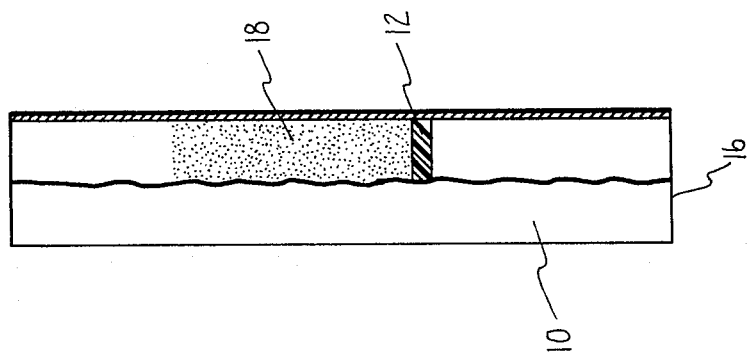
FIG. 3 illustrates the piece of heat shrinkable tubing of FIG. 2 after the placement of packing material therein.

FIGS. 1–5 illustrate the sequence of steps used for making a cartridge in accordance with the invention. FIG. 1 illustrates a piece of heat shrinkable tubing 10 prior to the placement of solid porous retainers 12 and 14 (FIGS. 2–5) and packing 18 (FIGS. 3–5) therein. The individual retainers 12 and 14 are made from a solid porous material. FIG. 2 illustrates the tubing 10 after the placement of retainer 12 therein nearest end 16. FIG. 3 illustrates the tubing 10 after the placement of packing material 18 therein. The end of tubing 16 may be tapped to promote settlement of the packing material. FIG. 4 illustrates tubing 10 after the placement of retainer 14 therein nearest end 20. Retainer 14 may be pressed toward retainer 12 to cause contact between the packing material and the retainers 12 and 14. FIG. 5 illustrates the completed cartridge 22 after heat shrinkage of tubing 10. The reduced diameter ends 16 and 20 form openings to the cartridge.

It may be desirable to fuse the tubing 10 and the retainers 12 and 14 at the interfaces 24 and 26 by the application of a sufficient amount of heat to the tubing during its heat shrinkage. Fusion of the tubing 10 and the retainers 12 and 14 produces an effective fluid seal at the interfaces 24 and 26.

It may also be desirable to make the inlet 20 and outlet 16 of different lengths to designate the direction of fluid flow through the cartridge or to provide sufficient length to couple the cartridge to fluid delivery or collection systems.

One method which can be used to prepare several cartridges at the same time is the following. Several pieces of heat-shrinkable tubing are placed to a fixed depth over bullet-shaped hollow mandrils on a vertical rack. A polytetrafluoroethylene rod having an outside diameter somewhat smaller than the diameter recovered inside diameter of the inlet and outlet openings of the cartridge and an overall length more than twice the length of the mandril is placed inside each of the hollow mandrils such that the upper end of the rod is flush with the tip of the mandril. A vacuum device having finger-like members is then used to pick up as many retainers as there are mandrils and deposit one retainer inside each piece of heat-shrinkable tubing. When the vacuum is released, the retainers are pressed squarely into place against the tip of each mandril. A second vacuum device then picks up several fixed volumes of packing material and deposits one volume into each piece of heat-shrinkable tubing on top of the retainer. The entire rack is then briefly tapped manually to slightly settle the packing material. The first vacuum device then is used to pick up the second series of retainers, deposit one in each piece of tubing, and after release of the vacuum, to press the retainers snugly against the top of the packing material. A second short polytetrafluoroethylene rod having an outside diameter somewhat smaller than the desired recovered inside diameter of the inlet and outlet openings of the cartridge is then inserted tip down into each piece of tubing as a vertical guide pin. The lower set of hollow mandrils are moved down and out of the heat-shrinkable tubing so that the lower retainers rest on the tips of the polytetrafluoroethylene rods which continue to extend within the pieces of tubing.

A conveyor belt then carries the entire apparatus through an oven for a period of about 6 seconds during which time the heat-shrinkable tubing shrinks tightly around the retainer and packing material while being loosely supported vertically by the polytetrafluoroethylene rods. Following heating in the oven the cartridges are cooled and then removed from the ends of the polytetrafluoroethylene rods and resemble the cartridge shown in the accompanying FIG. 5.

A more complete appreciation of the invention will be realized by reference to the following specific examples relating to a specific cartridge and process for utilization of that cartridge. The following examples are not intended to limit the invention disclosed herein except to the extent that limitations are specifically stated or to the extent to which limitations appear in the appended claims.

EXAMPLE 1

A sample preparation cartridge was prepared from a 5.5 cm. length of heat-shrinkable, irradiated, cross-linked, low density polyethylene tubing having a 0.375 inch I.D. in expanded form, grade FP-301 clear, obtained from Electronized Chemical Corp. of Burlington, Mass. A 1/16 inch thick sheet of high-density polyethylene having a porosity of 35 microns was obtained from Porex Plastics in Fairburn, Ga. and two disks about 1 cm. in diameter were cut out of the sheet with a die cutter. One of the disk-shaped retainers was placed into one end of the tubing about 1.5 cm. from the end. About 0.6 gram of silica gel chromatographic packing material, 55–105 microns in size, was dropped into the tubing which was tapped briefly to settle the packing slightly. The second disk-shaped retainer was then placed into the tubing and pressed snugly against the surface of the packing material. The assembled cartridge was then heated in an oven to a temperature of 120°-125° C. for approximately two minutes. The heated tubing shrunk tightly around the retainer and packing material, radially and longitudinally compressing the packing into a tightly packed bed. The ends of the tubing which extend beyond the retainers shrunk sufficiently so that they formed end fittings for the packed bed allowing the tip of a standard Luer tip syringe to be pressed snugly into the end of the cartridge.

EXAMPLE 2

The sample preparation cartridge prepared in Example 1 above was then used to isolate and partially purify the fat soluble vitamins A-palmitate, E-acetate, and $D_2$ or $D_3$, found in ready-to-eat breakfast cereals and animal feeds. Initially, 14 grams of Kellogg's Product 19 dry cereal was weighed into a container and homogenized in the non-polar solvent, hexane. Then, 10 milliliters of this extract was pumped through the cartridge. The packed bed retained the fat soluble vitamins present in the cereal extract with any other polar components extracted by the hexane. Very non-polar components were eluted friom the bed. The retainer held back small particles of cereal grain, thus effecting sample filtration as well.

The milliliters of a 50:50 mixture of hexane:ethyl acetate was then passed through the cartridge and the eluent was collected in a small test tube. The solvent mixture selectively eluted the fat soluble vitamins and the packed silica bed retained the very polar components in the sample. The vitamins were then in a volume of only 2 milliliters, a five-fold concentration from the initial concentration in the hexane extract.

Ten microliters of the eluate were then injected into a $\mu$-Bondapak (a Waters Associates trademark) column which separated and allowed quantitation of A-palmitate, E-acetate, and D.

EXAMPLE 3

A sample preparation cartridge as prepared in Example 1 above was then used to isolate and partially purify the carbamate pesticides Methomyl and Oxamyl from a collard greens sample. A 20 gram sample of frozen collard greens was weighed into a container and homogenized in the medium polarity solvent, dichloromethane. The extract was gravity filtered to remove fibers and 5 milliliters of this extract was pumped through the cartridge. The packed bed retained the pesticides present in the extract along with other more polar components. The non-polar components were eluted from the bed with an additional two milliliters of dichloromethane. The retainer filtered small particles from the extract, thus effecting sample filtration.

Then 2 milliliters of a 10:90 mixture of methanol:dichloromethane was passed through the cartridge to selectively elute the pesticides from the bed. The eluent was collected in a small test tube. In this manner the pesticides were freed from the vegetable substrate and concentrated.

The eluent was then evaporated to dryness and the residue redissolved in the appropriate mobile phase for chromatographic analysis and quantitation.

We claim:
1. A chromatography cartridge comprising:
    a volume of particulate chromatographic packing material, said volume having
        a first surface through which fluid enters during use,
        a second surface through which fluid exits during use,
            said first and second surfaces being substantially normal to an axial flow direction, and
        a third surface with normals extending in generally radial directions perpendicular to the axial direction,
    a first porous element contacting said first surface
    a second porous element contacting said second surface,
    a tube of solid heat-shrinkable plastic material shrunk
        so as to fit tightly around said third surface of said volume and thereby radially compress said bed and
        so as to fit tightly around portions of said first and second porous element to urge said porous elements toward each other to thereby axially compress said packing material,
        said heat shrunk tube extending axially beyond said porous elements with a cross-sectional area less than that of said porous elements to form an inlet and outlet for said cartridge.
2. The cartridge as defined in claim 1 wherein the heat-shrinkable tubing is made of polyolefin.
3. The cartridge of claim 2 wherein the polyolefin is crosslinked polyethylene.
4. The cartridge as defined in claim 1 wherein the porous elements are high density polyethylene.
5. The cartridge as defined in claim 1 wherein the volume of the packing material is generally cylindrical in shape.
6. The cartridge as defined in claim 1 wherein said packing is liquid chromatographic packing.
7. A process for preparing the chromatographic cartridge of claim 1, comprising:
    (a) placing a volume of chromatographic particulate packing material through which fluid is to flow within a piece of heat-shrinkable solid plastic tubing,
    (b) recessing a first porous element within the tubing so that it is adjacent to the surface of the volume through which fluid is to enter the volume,
    (c) recessing a second porous element within the tubing so that it is adjacent to the surface of the volume through which fluid is to exit from the volume,
    (d) heating the piece of tubing containing the packing material and pieces of solid porous material to shrink the tubing tightly around said volume, to radially compress said packing material, and tightly around portions of said first and second porous elements to urge said porous elements toward each other, to axially compress said packing material, and to form an inlet opening to and an outlet opening from the packed bed.
8. The process as defined in claim 7 wherein the heat-shrinkable tubing is made of a polyolefin.
9. The process as defined in claim 8 wherein the polyolefin is crosslinked polyethylene.
10. The process as defined in claim 7 wherein the porous elements are high density polyethylene.
11. The process as defined in claim 7 wherein the volume of the packing material is generally cylindrical in shape.
12. A process as defined in claim 7 wherein the packing is liquid chromatographic packing.

* * * * *

UNITED STATES PATENT AND TRADEMARK OFFICE
CERTIFICATE OF CORRECTION

PATENT NO. : 4,211,658
DATED : July 8, 1980
INVENTOR(S) : Patrick D. McDonald et al.

It is certified that error appears in the above-identified patent and that said Letters Patent are hereby corrected as shown below:

In the references cited, "Mochizuki et al. 4,059,526" is changed to --Mochizuki et al. 4,059,523--.

In the abstract, line 4, "though which" is changed to --through which--.

In the abstract, line 8, "compress the" is changed to --compresses the--.

Column 3, line 4, "comression" is changed to --compression--.

Column 5, line 26, "smplify" is changed to --simplify--.

Column 6, line 9, "than the diameter" is changed to --than the desired--.

Column 7, line 27, "friom" is changed to --from--.

Column 7, line 30, "The milliliters" is changed to --Two milliliters--.

Signed and Sealed this

Fourth Day of November 1980

[SEAL]

Attest:

SIDNEY A. DIAMOND

Attesting Officer

Commissioner of Patents and Trademark